(12) United States Patent
Goodman et al.

(10) Patent No.: US 9,039,744 B2
(45) Date of Patent: May 26, 2015

(54) SPINAL PLATE ASSEMBLY

(71) Applicant: Beacon Biomedical, LLC, Jupiter, FL (US)

(72) Inventors: Chris Goodman, Tequesta, FL (US); Dale Mitchell, Jupiter, FL (US); Tawney Schwarz, Jupiter, FL (US)

(73) Assignee: Beacon Biomedical, LLC, Jupiter, FL (US)

( * ) Notice: Subject to any disclaimer, the term of this patent is extended or adjusted under 35 U.S.C. 154(b) by 173 days.

(21) Appl. No.: 13/645,059

(22) Filed: Oct. 4, 2012

(65) Prior Publication Data

US 2013/0085532 A1    Apr. 4, 2013

Related U.S. Application Data

(60) Provisional application No. 61/542,873, filed on Oct. 4, 2011.

(51) Int. Cl.
*A61B 17/80* (2006.01)
*A61B 17/70* (2006.01)

(52) U.S. Cl.
CPC ......... *A61B 17/7059* (2013.01); *A61B 17/7061* (2013.01); *A61B 17/8033* (2013.01); *A61B 17/8042* (2013.01)

(58) Field of Classification Search
CPC ................ A61B 17/7061; A61B 17/8033
USPC ................................... 606/246, 289
See application file for complete search history.

(56) References Cited

U.S. PATENT DOCUMENTS

| | | | |
|---|---|---|---|
| 6,361,537 B1 * | 3/2002 | Anderson | 606/86 B |
| 6,533,786 B1 * | 3/2003 | Needham et al. | 606/282 |
| 6,755,833 B1 | 6/2004 | Paul et al. | |
| 7,008,426 B2 * | 3/2006 | Paul | 606/70 |
| 7,070,599 B2 | 7/2006 | Paul | |
| 7,204,837 B2 * | 4/2007 | Paul | 606/276 |
| 7,255,699 B2 | 8/2007 | Paul | |
| 8,128,668 B2 * | 3/2012 | Paul | 606/294 |
| 8,216,285 B2 * | 7/2012 | Markworth | 606/294 |
| 8,470,006 B2 * | 6/2013 | Paul | 606/294 |
| 2004/0030338 A1 | 2/2004 | Paul | |

FOREIGN PATENT DOCUMENTS

| | | | | |
|---|---|---|---|---|
| FR | 2778088 | 11/1999 | | |
| WO | WO 2006098906 A1 * | 9/2006 | | |
| WO | WO 2010054181 A1 * | 5/2010 | | A61B 17/80 |

* cited by examiner

*Primary Examiner* — Ellen C Hammond
(74) *Attorney, Agent, or Firm* — McHale & Slavin P.A.

(57) ABSTRACT

The present invention is directed to implantable devices for stabilizing or fusing bone structures within the spine. More specifically, the present invention is a spinal plate assembly that includes an automatic mechanism for blocking the pathway of a bone fastener once inserted to prevent unwanted backwards migration of the bone screw.

19 Claims, 9 Drawing Sheets

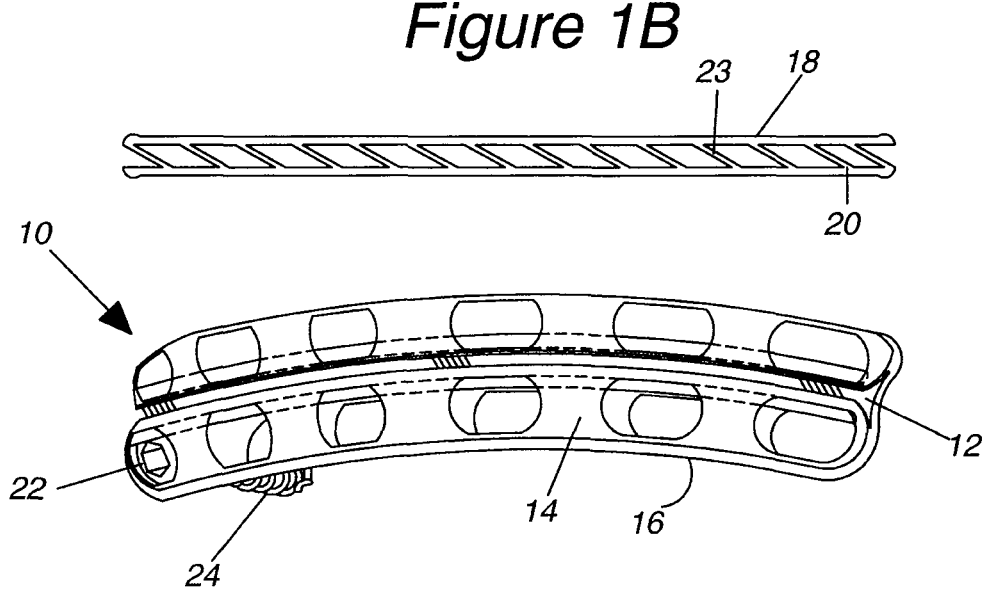
Figure 1B
Prior Art
Figure 1A

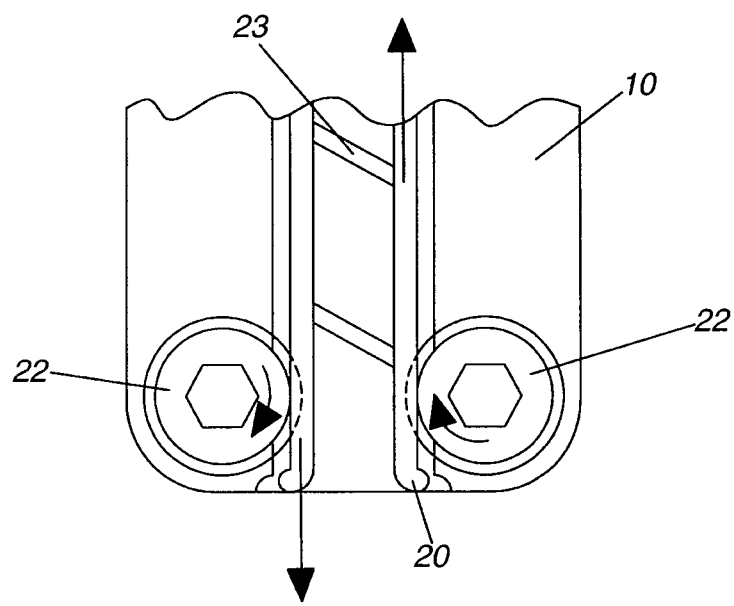
*Prior Art*
*Figure 2*

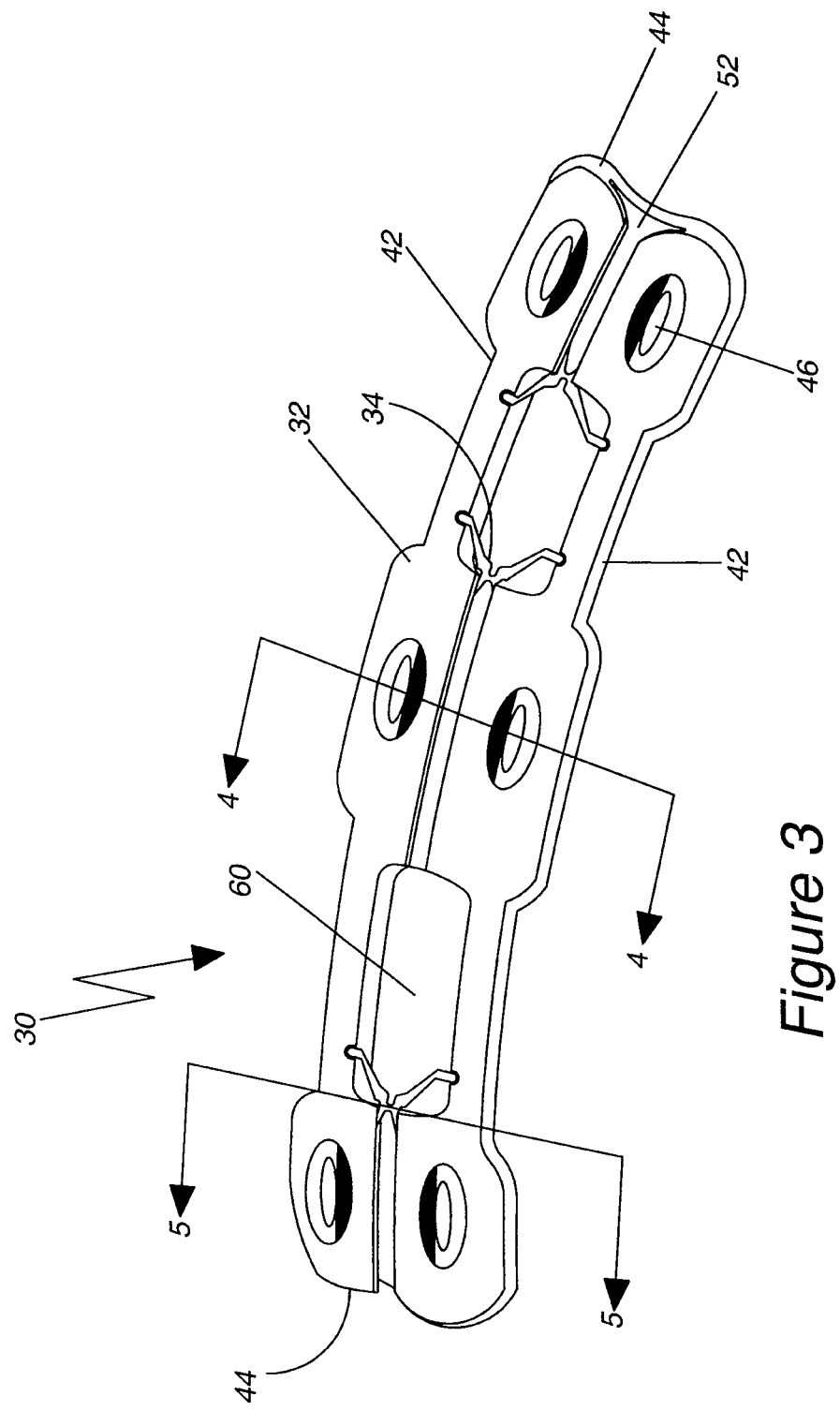
Figure 3

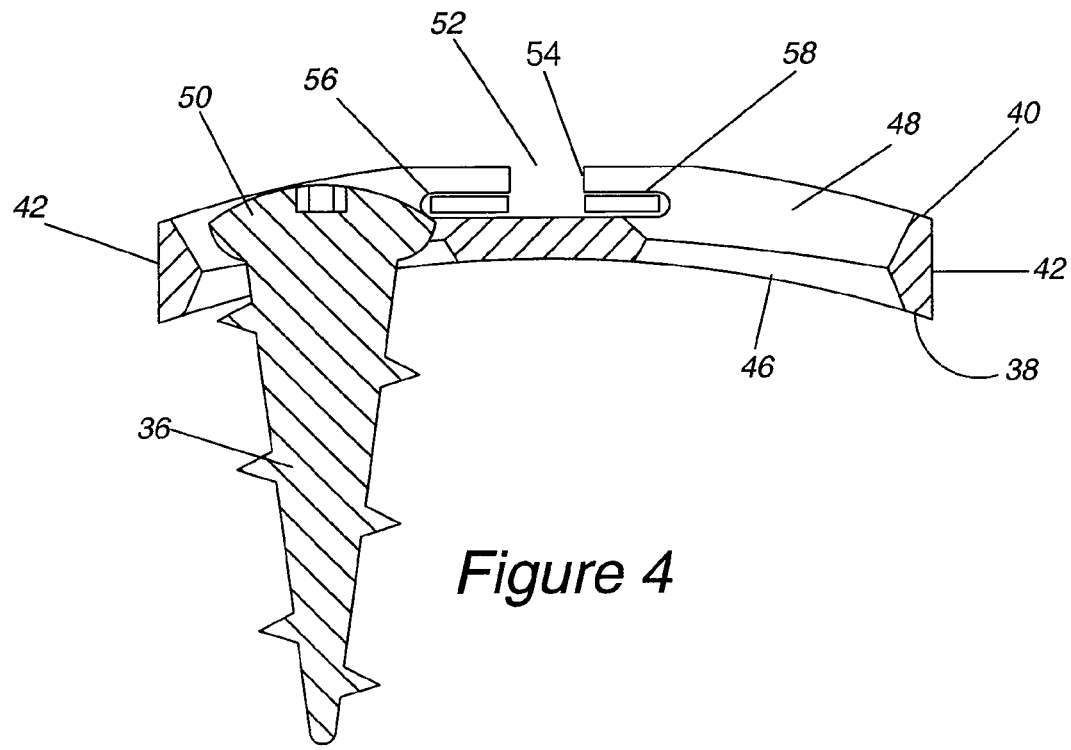
Figure 4
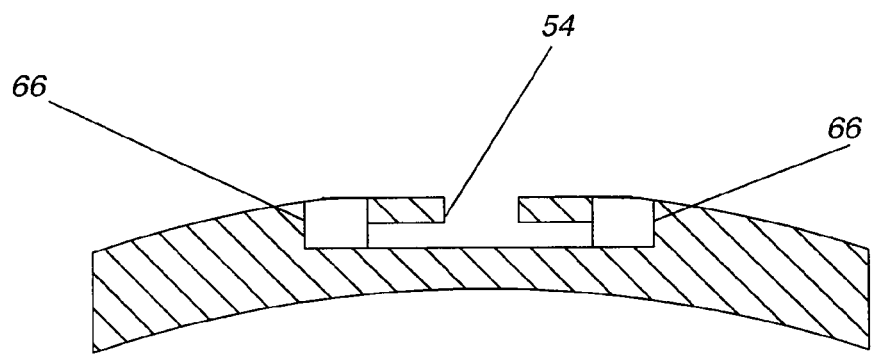
Figure 5

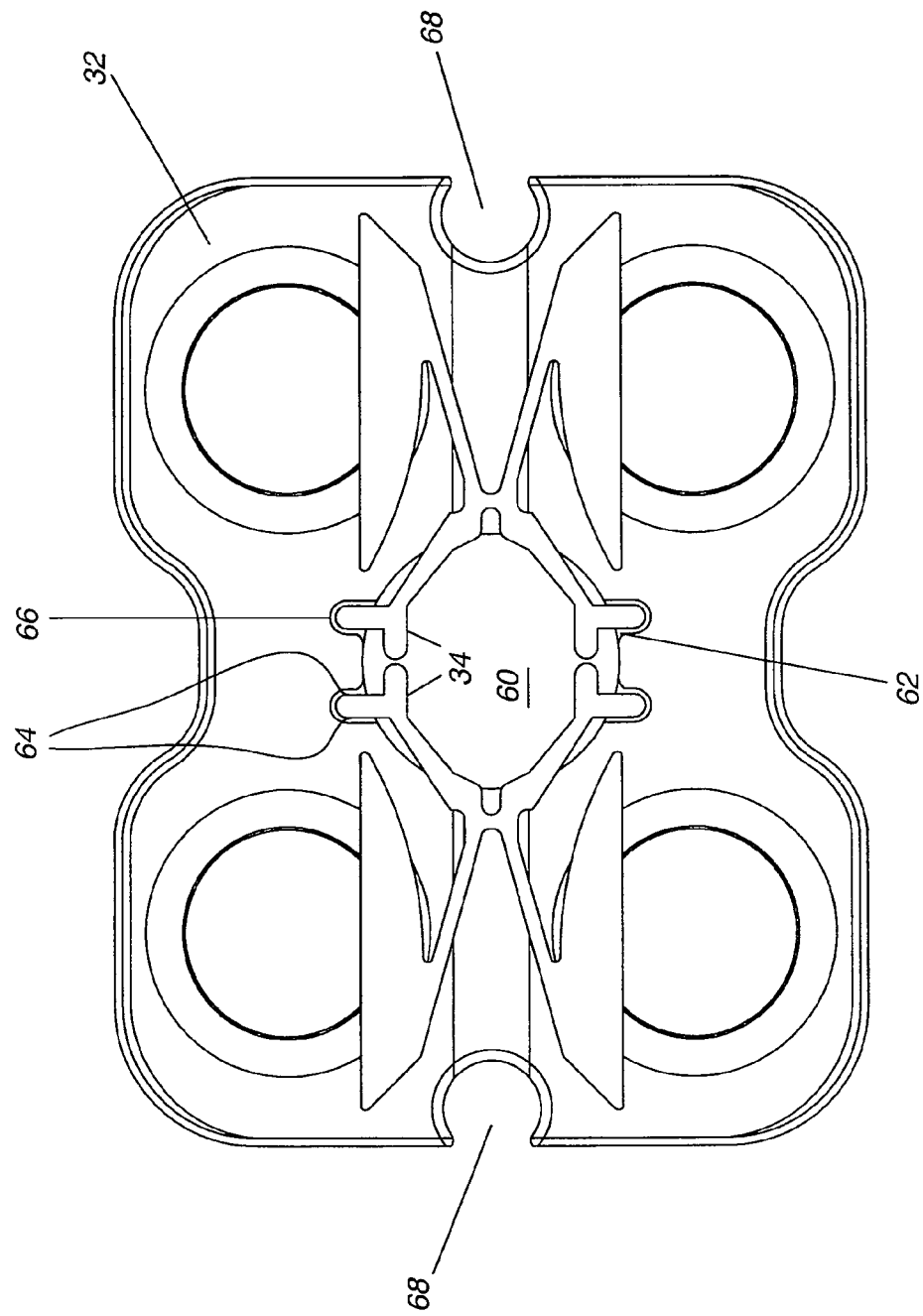
Figure 6

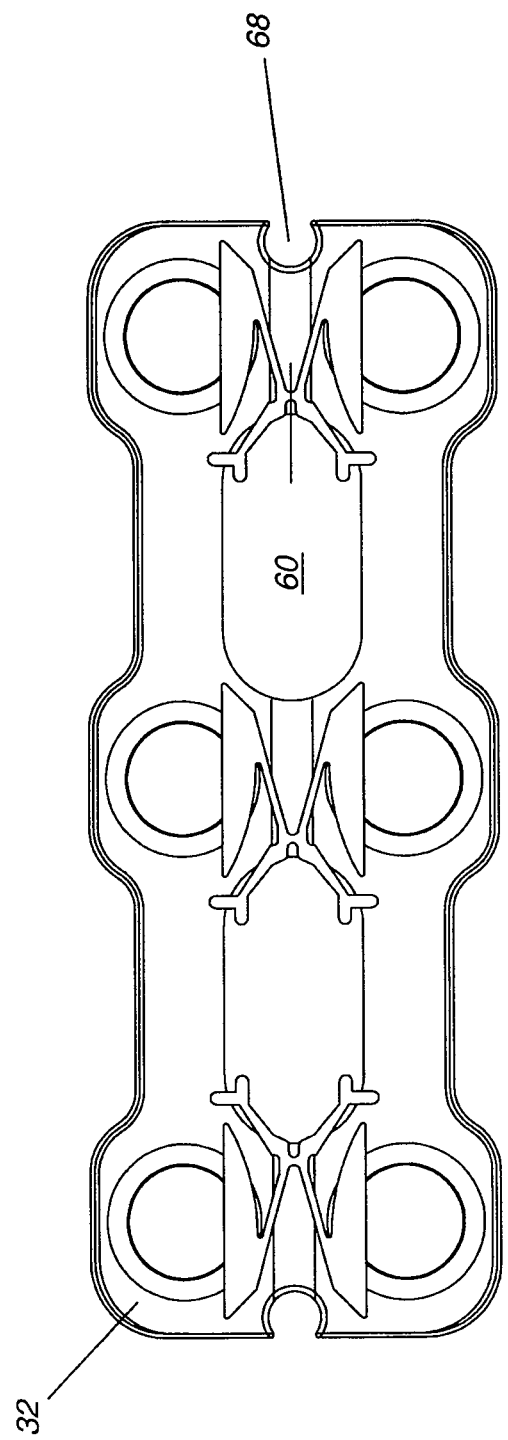
Figure 7A

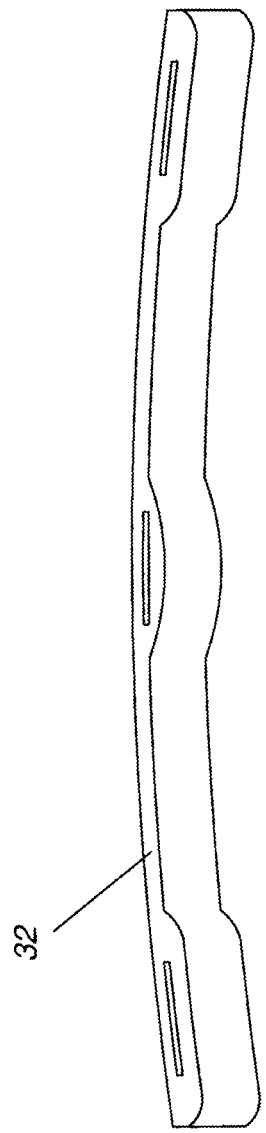
Figure 7B

Figure 9
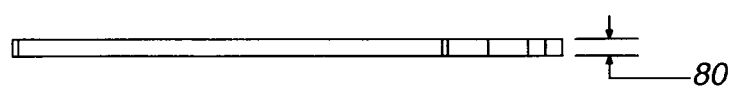
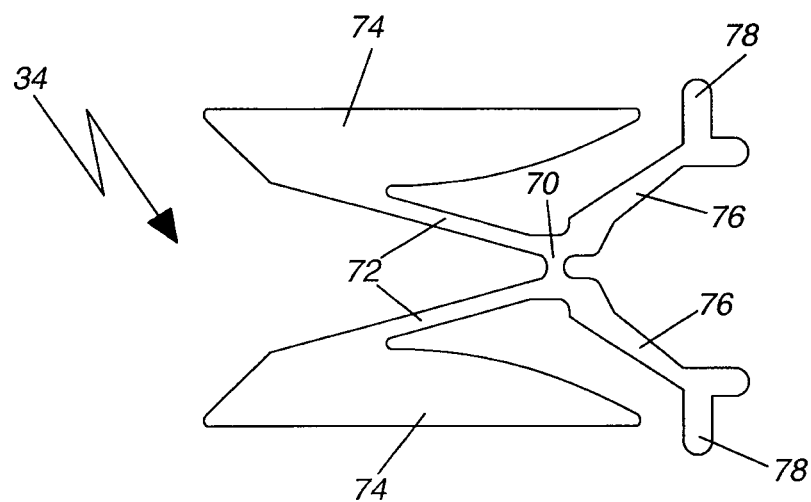
Figure 8

Figure 11
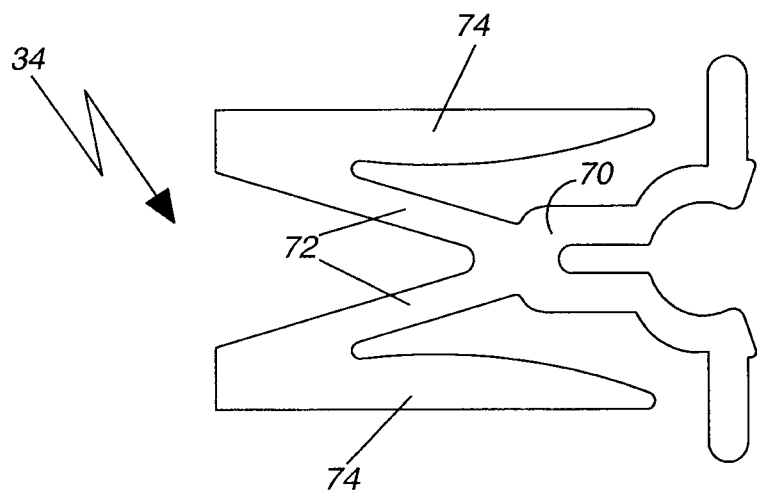
Figure 10

SPINAL PLATE ASSEMBLY

REFERENCE TO RELATED APPLICATIONS

In accordance with 37 C.F.R 1.76, a claim of priority is included in an Application Data Sheet filed concurrently herewith. Accordingly, the present invention claims priority under 35 U.S.C. §119(e), 120, 121, and/or 365(c) to U.S. Provisional Patent Application No. 61/542,873, entitled, "SPINAL PLATE ASSEMBLY", filed on Oct. 4, 2011. The contents of each of the above referenced applications are herein incorporated by reference in its entirety.

FIELD OF THE INVENTION

The present invention relates to instruments and methods for the fixation and/or stabilization of spinal bones. More specifically, the present invention relates to a spinal plate assembly for fixation and/or stabilization of spinal column bones. The spinal plate includes a blocking mechanism that prevents unwanted backing out of the screws utilized to secure the plate to the bone(s) once installed.

BACKGROUND OF THE INVENTION

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The anulus of the disc forms the disc perimeter, and is a tough, outer fibrous ring that binds adjacent vertebrae together. The fiber layers of the anulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction. It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases it is desired to fuse the adjacent vertebrae together after removal of the disc, sometimes referred to as "intervertebral fusion" or "interbody fusion." In this process, spondylodesis or spondylosyndesis is used to join two or more vertebrae to eliminate pain caused by abnormal motion, degradation, fractures or deformities of the vertebrae.

Spinal plates have become one common approach to attaching one adjacent vertebra to another. A spinal plate generally includes an elongated plate of a metal such as titanium or stainless steel. The plate includes a plurality of apertures positioned to allow a surgeon to attach the plate across at least two vertebras with screws. The combination of the plate and screws serve to hold the adjacent vertebra together while the intervertebral fusion occurs.

One shortcoming to this approach relates to the screws utilized to hold the plate to the bone. As the person who had the plate installed continues with his/her everyday life, the plate is repeatedly loaded and twisted. Each motion that the person makes applies a dynamic load to both the screws and the plate. This repeated loading and unloading places tremendous stress on the plate and particularly on the screws that interface with the soft bone. These stresses tend to cause the screws to back out of the bone over time. The backing out of the screws can cause complications that not only affect the fusion of the bone, but may also damage nerves and tissues in the proximity of the implant. Additional issues such as osteoporosis may exacerbate the problem. Additional surgeries may therefore be required to repair or remove loosened screws or implants.

A number of plate assembly designs have been proposed in attempts to prevent screws from pulling away or withdrawing from the bone and/or to prevent the screws from backing out, pulling away or withdrawing from the surface of the spinal plate. Some of these devices include rotating or sliding plates that cover a top surface of the screw. Other devices include set screws that apply pressure to the top of the screw. All of these devices require secondary action by the surgeon to activate or set the mechanisms that prevent the screws from backing out. Because the parts are very small, the risk of losing a part into the patient or improperly assembling the locking devices is unreasonably high.

Another type of system for preventing screw back out includes springs that automatically snap over a portion of the bone screw as it is inserted into the plate and thus the bone. For example, U.S. Pat. Nos. 7,008,426, 7,070,599, and 7,204,837 disclose a bone plate having an elongated slot extending the length of the plate between the top and bottom surfaces of the plate. A pair of elongated strips of material are positioned within the slot with springs therebetween to force the strips toward the outer portions of the slot. The slot and the strips are positioned to require movement of one of the strips as the head portion of the bone screws enter the plate.

A shortcoming to this type of device relates to longitudinal movement of the strips during insertion of the bone screws. As designed, the screw head was intended to pass the strip and force it medially with respect to the plate and snap back to cover a portion of the screw to prevent the screw from backing out after the screw head passed the strip. However, in practice a surgeon will generally install all of the screws partially into the bone. An x-ray is then taken to assure the proper positioning of the screws before they are finally tightened. Because partial placement of the screws causes both strips to move medially at the same time with respect to the plate, the strips lose contact with the plate, causing them to be free for longitudinal movement. Because the spring pressure causes the strip to bear against the side of the screws, rotation of any of the screws causes displacement of the strips longitudinally with respect to the plate. This movement prevents the strips from functioning for their intended purpose and requires the plate to be removed from the patient.

A further shortcoming to this device is the locking strips prevent windows from being positioned in the plate to allow visualization through the plate. This construction makes positioning of the plate more difficult for the surgeon.

Therefore, there is a need in the art for a spinal plate that includes a locking mechanism that allows increased versatility in screw placement. The locking mechanism should operate automatically, e.g. without manual manipulation of the locking mechanism, as any number of screws are secured to bone through the plate to positively prevent back out of the bone screw(s). The locking mechanism should also allow for partial insertion of the bone screws without longitudinal displacement of the locking mechanism.

SUMMARY OF THE INVENTION

The present invention is directed to implantable devices for stabilizing or fusing bone structures within the spine. More specifically, the present invention is a spinal plate assembly that includes an automatic mechanism for blocking the pathway of a bone fastener once inserted to prevent unwanted backwards migration of the bone screw. The automatic mechanism generally includes a central base portion, a pair of spring loaded blades and a pair of anchors. The central base portion is substantially rigid having a pair of leaf type springs extending outwardly therefrom; each left type spring having a blade member mounted on a distal end thereof. The central base portion also includes a second pair of leaf springs extending outwardly therefrom in an opposite direction with respect to the first leaf springs. A pair of anchor members are secured to the distal ends of the second pair of leaf springs to engage pockets formed into the bone plate. In this manner, each spring loaded blade may be operated independently or simultaneously without dislodging the connection between the anchors and the bone plate.

Accordingly, it is an objective of the instant invention to provide a spinal plate for stabilization and/or fusion of adjacently positioned spinal bones.

It is a further objective of the instant invention to provide a spinal plate that includes an automatically operating screw locking mechanism for preventing screws from backing out of position once properly seated within the spinal plate.

It is yet another objective of the instant invention to provide a spinal plate that includes a locking mechanism that includes two locking blades connected to a central base via independent spring members so that the blades can function individually or simultaneously.

It is a still further objective of the invention to provide a spinal plate that includes a locking mechanism that includes two anchor members connected to a central base via independent spring members so that the anchors remain independent with respect to operation of the locking blades to prevent dislodgement of the locking mechanism during operation thereof.

It is still yet another objective of the invention to provide a spinal plate with a locking mechanism wherein the spinal plate includes windows for visualization through the plate.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1A is a perspective view of a prior art bone plate with locking member in place;

FIG. 1B is a perspective view of the locking member of the prior art illustrated in FIG. 1A;

FIG. 2 is a partial view of the embodiment illustrated in FIG. 1A illustrating one shortcoming of the design;

FIG. 3 is a perspective view of one embodiment of the present invention illustrated with multiple locking mechanisms in place;

FIG. 4 is a partial section view taken along lines 4-4 of FIG. 3;

FIG. 5 is a partial section view taken along lines 5-5 of FIG. 3;

FIG. 6 is a top view partially in phantom illustrating one embodiment of the present invention;

FIG. 7A is a top view of the embodiment illustrated in FIG. 3;

FIG. 7B is a side view of the embodiment illustrated in FIG. 3;

FIG. 8 is a top view of one embodiment of the locking mechanism of the present invention;

FIG. 9 is a side view of the locking mechanism embodiment illustrated in FIG. 8;

FIG. 10 is a top view of one embodiment of the locking mechanism of the present invention; and FIG. 11 is a side view of the locking mechanism embodiment illustrated in FIG. 10.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1A and 1B, a prior art spine plate assembly 10 is illustrated. The bone plate 10 includes an elongated slot 12 extending the length of the plate between the top 14 and bottom 16 surfaces of the plate. A member 18 including a pair of elongated strips 20 of material are positioned within the slot with springs 23 therebetween to force the strips toward the outer portions of the slot 12. The slot and the strips are positioned to require movement of one of the strips as the head portion 22 of the bone screws 24 enter the plate 10. A shortcoming to this type of device relates to longitudinal movement of the strips 20 during insertion of the bone screws 24. As designed, the screw head 22 was intended to pass the strip 20 to force the strip medially with respect to the plate 10 and snap back to cover a portion of the screw to prevent the screw from backing out after the screw head passed the strip. However, in practice a surgeon will generally install all of the screws partially into the bone. An x-ray is then taken to assure the proper positioning of the screws 24 before they are finally tightened. Partial placement of the screws causes both strips 20 to move medially at the same time, as illustrated in FIG. 2; the strips 20, therefore, lose contact with the plate 10 causing the strips to be free for longitudinal movement. The spring pressure causes the strip to bear against the side surface of the screw head 22, whereby rotation of any of the screws causes displacement of the strips longitudinally with respect to the plate. This movement prevents the strips from functioning for their intended purpose and requires the plate to be removed from the patient for replacement with another device. A further shortcoming to this type of device relates further to the elongated locking strips. The elongated locking strips extend the full length of the plate. This construction prevents sight windows from being positioned in the plate between the bone apertures to allow visualization through the plate. The lack of sight windows makes positioning of the plate more difficult for the surgeon.

Referring to FIGS. 3-7, a spinal plate assembly 30 is illustrated. The spine plate assembly 30 generally includes a spine plate 32, a locking member 34 and a plurality of bone screws 36. The spine plate 32 is preferably constructed from a biocompatible material such as titanium, and includes a bottom surface 38, a top surface 40, a pair of side surfaces 42 and a pair of end surfaces 44. At least two bores 46 extend through the top and bottom surfaces 38, 40, each of the bores are sized for passage of a bone screw 36. In addition, each bore 46 includes a counterbore 48 extending downwardly from the top surface 40. The counterbore is sized and shaped to substantially contain a head portion 50 of the bone screw. The counterbore may be of any shape desirable to match with the bone screw. For example, the counter bore may be spherical, square, truncated or any suitable combination thereof. A segmented T-slot 52 extends between the pair of end surfaces 44 and substantially parallel to the top surface 40. A first leg 54 of the T-slot extends through the top surface 40 while portions of the second and third legs 56, 58 extend into each counterbore 48. The segments of the T-slot 52 are separated by sight windows 60 extending between the top and bottom surfaces. The sight windows 60 aid the surgeon in placement of the spinal plate 32 by allowing the surgeon to view anatomical features through the plate. The spinal plate also preferably includes at least one, and more preferably two anchor pockets 62. The anchor pockets are generally constructed and arranged to cooperate with a portion of the locking member 34 to secure the locking member to the spinal plate. The anchor pockets 62 extend downward from the top surface 40 to about the same depth as the second and third legs 56, 58 of the T-slot 52 and are wider than the T-slot 52 when viewed from an end surface 44 of the spinal plate 32. The anchor pockets 62 include side surfaces 64 and end surfaces 66 which cooperate with the locking member 34. The spinal plate 32 may additionally include tool apertures 68 which aid in the placement of the plate. The tool apertures 68 are preferably sized for cooperation with a gripping tool or K-wire, whereby the plate may be more easily maneuvered into position within the anatomy of a human or animal in vivo. The tool aperture may additionally function as windows for the surgeon once the plate has been maneuvered into position.

Referring to FIGS. 3-11, a locking member 34 is illustrated. The locking member is generally constructed and arranged to fit substantially within the T-slot 52 with portions extending into the counterbores 48 for blocking backwards migration of the bone screws 36 after insertion. The locking member includes a central base portion 70 having at least one, and more preferably two leaf springs 72 extending outwardly therefrom in a first direction. A blade portion 74 is secured to a distal end of each leaf spring 72 to contact the first side wall of the second leg of the T-slot 52 whereby a portion of each blade 74 extends into at least one counterbore 48. At least one and more preferably two anchor portions 76 extend outwardly from the base portion in a direction different from the leaf spring 72. Each anchor portion 76 terminates in an anchor foot 78 whereby each anchor foot 78 is constructed and arranged to fit into a respective anchor pocket 62. The anchor foot 78 cooperates with the pair of anchor pocket side walls 64 and end wall 66 to prevent movement of the locking member during movement of the blade portion away from the side surfaces of the second and third legs 56, 58 of the T-slot 52. In at least one embodiment, the anchor portion is constructed to function as a leaf spring and may further be constructed to apply a preload force to the side and/or end surfaces of the anchor pocket to further secure the locking member to the spinal plate. The locking member 34 is preferably constructed from a relatively thin biocompatible material, such as but not limited to Nitinol, having a spring temper. In one embodiment, the thickness 80 of the locking member is about 0.015 thousandths of an inch.

Referring to FIGS. 3, 6 and 7, spinal plates 32 having different lengths are illustrated. As shown in FIG. 6, an embodiment is illustrated having two sets of through bores 46. It should be appreciated that each set of through bores include one locking member 34. This construction permits the same locking member construction to be utilized across an entire series of spinal plates having different lengths and different number of through bores.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as, those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal plate assembly comprising:
   a spinal plate, said spinal plate including a bottom surface, a top surface, a pair of side surfaces and a pair of end surfaces, at least two bores extending through said top and said bottom surfaces, each of said bores sized for passage of a bone screw, each of said bores including a counterbore extending downwardly from said top surface, said counterbore sized and shaped to substantially contain a head portion of said bone screw, a segmented T-slot extending between said pair of end surfaces and substantially parallel to said top surface, said T-slot extending through said top surface and into each said counterbore along first and second side surfaces thereof, at least one anchor pocket extending downward from said top surface, said anchor pocket having a pair of anchor pocket side walls, a locking member constructed and arranged to fit substantially within said T-slot, said locking member including a substantially rigid central base portion, at least one leaf spring extending outwardly therefrom in a first direction, a blade portion secured to a distal end of said leaf spring to contact a first side wall of said T-slot whereby said blade portion extends into at least one said counterbore to engage at least one said bone screw, at least one anchor portion extending outwardly from said base portion in a direction different from said leaf spring, said at least one anchor portion terminating in an anchor foot, said anchor foot being constructed and arranged to fit into said at least one anchor pocket whereby a portion of said anchor foot contacts said pair of anchor pocket side walls to prevent movement of said central base portion along said T-slot during movement of said blade portion away from said first side wall of said T-slot.

2. The spinal plate assembly of claim 1 wherein said locking member includes two diverging leaf springs extending outwardly from said central base portion, a blade portion secured to the distal end of each said leaf spring so that a first of said blade portions contacts said first side wall of said T-slot, a second of said blade portions contacting a second opposite side wall of said T-slot and extending into a second counterbore of said at least two bores.

3. The spinal plate assembly of claim 2 wherein said spinal plate includes two sets of at least two bores, each set of at least two bores each having a respective locking member, whereby each said bore cooperates with a respective locking blade.

4. The spinal plate assembly of claim 2 wherein said spinal plate includes three sets of at least two bores, each set of at least two bores each having a respective locking member, whereby each said bore cooperates with a respective locking blade.

5. The spinal plate assembly of claim 2 wherein said spinal plate includes four sets of at least two bores, each set of at least two bores each having a respective locking member, whereby each said bore cooperates with a respective locking blade.

6. The spinal plate assembly of claim 1 including a pair of anchor portions each terminating in an anchor foot, each said anchor foot being constructed and arranged to fit into an anchor pocket and cooperate with a pair of anchor pocket side walls to prevent movement of said locking member during movement of each said blade portion away from a respective side wall of said T-slot.

7. The spinal plate assembly of claim 6 wherein each said anchor portion includes an anchor leaf spring, said anchor leaf spring being constructed and arranged to apply pressure to oppositely positioned anchor pocket end walls.

8. The spinal plate assembly of claim 6 wherein each said blade portion is sufficiently elongate to extend across said portion of said counterbore along said first and said second T-slot side walls.

9. The spinal plate assembly of claim 1 wherein said bottom surface of said spinal plate is spherically concave.

10. The spinal plate assembly of claim 1 wherein said spinal plate includes at least one window extending between said top surface and said bottom surface.

11. A spinal plate kit comprising:
a spinal plate, said spinal plate including a bottom surface, a top surface, a pair of side surfaces and a pair of end surfaces, at least two bores extending through said top and said bottom surfaces, each of said bores sized for passage of a bone screw, each of said bores including a counterbore extending downwardly from said top surface, said counterbore sized and shaped to substantially contain a head portion of said bone screw, a T-slot extending between said pair of end surfaces and substantially parallel to said top surface, said T-slot extending through said top surface and into each said counterbore along first and second side surfaces thereof, at least one anchor pocket extending downward from said top surface, said anchor pocket having a pair of anchor pocket side walls, a locking member constructed and arranged to fit substantially within said T-slot, said locking member including a substantially rigid central base portion, at least one leaf spring extending outwardly therefrom in a first direction, a blade portion secured to a distal end of said leaf spring to contact a first side wall of said T-slot whereby said blade portion extends into at least one said counterbore, at least one anchor portion extending outwardly from said base portion in a direction different from said leaf spring, said at least one anchor portion terminating in an anchor foot, said anchor foot being constructed and arranged to fit into said at least one anchor pocket and cooperate with said pair of anchor pocket side walls to prevent movement of said central base portion during movement of said blade portion away from said first side wall of said T-slot;

a pair of bone screws, each said bone screw including a shank portion and a head portion, said shank portion including helical threads constructed and arranged to cooperate with a bone structure, said head portion being larger in diameter than said shank portion, said head portion sized to fit into said counterbore.

12. The spinal plate kit of claim 11 wherein said locking member includes two diverging leaf springs extending outwardly from said central base portion, a blade portion secured to the distal end of each said leaf spring so that a first of said blade portions contacts said first side wall of said T-slot, a second of said blade portions contacting a second opposite side wall of said T-slot and extending into a second counterbore of said at least two bores.

13. The spinal plate kit of claim 12 wherein said spinal plate includes two sets of at least two bores;
two said locking members, one for each set of at least two bores, whereby each said bore cooperates with a respective locking blade;
four said bone screws.

14. The spinal plate kit of claim 12 wherein said spinal plate includes three sets of at least two bores;
three said locking members, one for each set of at least two bores, whereby each said bore cooperates with a respective locking blade;
six said bone screws.

15. The spinal plate assembly of claim 12 wherein said spinal plate includes four sets of at least two bores;
four said locking members, one for each said set of at least two bores, whereby each said bore cooperates with a respective locking blade;
eight said bone screws.

16. The spinal plate kit of claim 11 including a pair of anchor portions each terminating in an anchor foot, each said anchor foot being constructed and arranged to fit into an anchor pocket and cooperate with a pair of anchor pocket side walls to prevent movement of said locking member during movement of each said blade portion away from a respective side wall of said T-slot.

17. The spinal plate kit of claim 16 wherein each said anchor portion includes an anchor leaf spring, said anchor leaf spring being constructed and arranged to apply pressure to oppositely positioned anchor pocket end walls.

18. The spinal plate kit of claim 16 wherein each said blade portion is sufficiently elongate to extend across said portion of said counterbore along said first and said second T-slot side walls.

19. The spinal plate kit of claim 11 wherein said bottom surface of said spinal plate is spherically concave.

* * * * *